USO09456931B2

(12) United States Patent
Wang et al.

(10) Patent No.: US 9,456,931 B2
(45) Date of Patent: Oct. 4, 2016

(54) THERMOPLASTIC AND WATER-DISPERSIBLE INJECTION MOLDABLE MATERIALS AND ARTICLES

(71) Applicant: Kimberly-Clark Worldwide, Inc., Neenah, WI (US)

(72) Inventors: James H. Wang, Appleton, WI (US); Gregory J. Wideman, Menasha, WI (US); Alphonse Carl DeMarco, Greenville, WI (US); Austin Pickett, LaCrosse, WI (US); Mark M. Mleziva, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 181 days.

(21) Appl. No.: 14/092,087

(22) Filed: Nov. 27, 2013

(65) Prior Publication Data

US 2015/0148733 A1     May 28, 2015

(51) Int. Cl.
| | |
|---|---|
| *A61F 13/32* | (2006.01) |
| *A61F 13/26* | (2006.01) |
| *A61F 13/20* | (2006.01) |
| *B29C 45/00* | (2006.01) |

(Continued)

(52) U.S. Cl.
CPC ......... *A61F 13/266* (2013.01); *A61F 13/2097* (2013.01); *B29C 45/0001* (2013.01); *C08L 29/04* (2013.01); *B29K 2029/04* (2013.01); *B29K 2105/0038* (2013.01); *B29K 2105/0088* (2013.01); *B29K 2105/251* (2013.01); *B29K 2995/0062* (2013.01); *B29L 2023/00* (2013.01); *C08L 2205/025* (2013.01)

(58) Field of Classification Search
CPC .. C08L 29/04; C08L 2205/025; A61F 13/26; A61F 13/263; A61F 12/28; A61F 13/266
See application file for complete search history.

(56) References Cited

U.S. PATENT DOCUMENTS

| | | |
|---|---|---|
| 3,724,462 A | 4/1973 | Hanke |
| 3,882,869 A | 5/1975 | Hanke |

(Continued)

FOREIGN PATENT DOCUMENTS

| | | |
|---|---|---|
| EP | 0 635 545 A2 | 1/1995 |
| EP | 0 635 545 A3 | 1/1995 |

(Continued)

OTHER PUBLICATIONS

Related U.S. Patent Application Form.

(Continued)

*Primary Examiner* — Susan Su
(74) *Attorney, Agent, or Firm* — Dority & Manning, P.A.

(57) ABSTRACT

A tampon applicator that is water-sensitive (e.g., water-soluble, water-dispersible, etc.) in that it loses its integrity over time in the presence of water is provided. The tampon applicator can be discreetly disposed of in a toilet without the risk of clogging sewer pipes. The tampon applicator includes a molded thermoplastic composition containing at least one partially hydrolyzed polyvinyl alcohol a plasticizer. The desired water-sensitive characteristics of the tampon applicator may be achieved in the present invention by selectively controlling a variety of aspects of the thermoplastic composition from which the applicator is formed, such as the nature of the components employed, the relative amount of each component, the manner in which the composition is formed, and so forth.

21 Claims, 3 Drawing Sheets

(51) Int. Cl.
*C08L 29/04* (2006.01)
*B29K 29/00* (2006.01)
*B29K 105/00* (2006.01)
*B29L 23/00* (2006.01)

(56) References Cited

U.S. PATENT DOCUMENTS

| | | | |
|---|---|---|---|
| 4,372,311 A | 2/1983 | Potts | |
| 4,499,154 A | 2/1985 | James et al. | |
| 4,731,122 A | 3/1988 | Cortese et al. | |
| 4,900,299 A | 2/1990 | Webb | |
| 4,921,474 A | 5/1990 | Suzuki et al. | |
| 5,002,526 A | 3/1991 | Herring | |
| 5,102,465 A | 4/1992 | Lamond | |
| 5,350,354 A | 9/1994 | Billmers | |
| 5,367,003 A | 11/1994 | Petcavich | |
| 5,378,751 A | 1/1995 | Deibig et al. | |
| 5,389,068 A | 2/1995 | Keck | |
| 5,393,528 A * | 2/1995 | Staab | A61F 6/08 424/409 |
| 5,496,874 A | 3/1996 | Faass et al. | |
| 5,509,913 A | 4/1996 | Yeo | |
| 5,533,990 A * | 7/1996 | Yeo | A61F 13/28 604/12 |
| 5,695,868 A | 12/1997 | McCormack | |
| 5,738,646 A | 4/1998 | Fox et al. | |
| 5,804,653 A | 9/1998 | Weng | |
| 5,855,999 A | 1/1999 | McCormack | |
| 5,868,824 A | 2/1999 | Andersen et al. | |
| 5,902,262 A | 5/1999 | Bastioli et al. | |
| 5,910,520 A | 6/1999 | Dabi et al. | |
| 5,932,497 A | 8/1999 | Morman et al. | |
| 5,954,683 A | 9/1999 | Downs et al. | |
| 5,997,981 A | 12/1999 | McCormack et al. | |
| 6,015,764 A | 1/2000 | McCormack et al. | |
| 6,111,163 A | 8/2000 | McCormack et al. | |
| 6,123,996 A | 9/2000 | Larsson et al. | |
| 6,203,515 B1 | 3/2001 | Norquest | |
| 6,248,880 B1 | 6/2001 | Karlson | |
| 6,461,457 B1 | 10/2002 | Taylor et al. | |
| 6,639,066 B2 | 10/2003 | Boström et al. | |
| 6,706,942 B1 | 3/2004 | Zhao et al. | |
| 6,730,057 B2 | 5/2004 | Zhao et al. | |
| 6,787,156 B1 | 9/2004 | Bar-Shalom | |
| 7,713,253 B2 | 5/2010 | Osborn, III et al. | |
| 8,317,765 B2 | 11/2012 | Loyd et al. | |
| 8,458,882 B2 | 6/2013 | Mastalish et al. | |
| 8,569,402 B2 | 10/2013 | Henderson et al. | |
| 8,802,168 B2 | 8/2014 | Song et al. | |
| 2002/0042599 A1 | 4/2002 | Zhao et al. | |
| 2002/0183182 A1* | 12/2002 | Balzar | A61F 13/2082 493/269 |
| 2003/0036721 A1* | 2/2003 | Zhao | A61F 13/26 604/15 |
| 2003/0040695 A1 | 2/2003 | Zhao et al. | |
| 2003/0135180 A1 | 7/2003 | Nguyen et al. | |
| 2003/0232911 A1 | 12/2003 | Hwang et al. | |
| 2006/0016714 A1 | 1/2006 | Fregonese et al. | |
| 2006/0025541 A1 | 2/2006 | Bourgoin et al. | |
| 2007/0232982 A1 | 10/2007 | Jarmon et al. | |
| 2007/0276317 A1* | 11/2007 | Henderson | A61F 13/15211 604/15 |
| 2010/0016780 A1 | 1/2010 | VanDenBogart et al. | |
| 2010/0297458 A1 | 11/2010 | Khemani et al. | |
| 2011/0186467 A1* | 8/2011 | Denome | B65D 65/46 206/524.7 |
| 2011/0189413 A1* | 8/2011 | Denome | B65D 65/46 428/35.4 |
| 2011/0250241 A1 | 10/2011 | Duffield et al. | |
| 2012/0328804 A1 | 12/2012 | Allen et al. | |
| 2013/0281912 A1 | 10/2013 | Mikhail | |

FOREIGN PATENT DOCUMENTS

| | | |
|---|---|---|
| EP | 0 613 672 A1 | 5/2004 |
| WO | WO 96/04338 A1 | 2/1996 |
| WO | WO 00/15165 A1 | 3/2000 |
| WO | WO 02/085983 A1 | 10/2002 |
| WO | WO 2012/092671 A1 | 7/2012 |
| WO | WO 2013011301 A1 | 1/2013 |

OTHER PUBLICATIONS

International Search Report and Written Opinion for PCT/IB2014/064934 dated Jan. 26, 2015, 14 pages.
Technical Data Sheet from Kuraray-Poval for Exceval, 8 pages (undated).
Technical Data Sheet from Kremer Pigmente GmbH & Co. For 6370063712,Klucel®, Hydropropylcellulose, 2 pages (undated).

* cited by examiner

THERMOPLASTIC AND WATER-DISPERSIBLE INJECTION MOLDABLE MATERIALS AND ARTICLES

BACKGROUND OF THE INVENTION

Flushable feminine care products provide consumers with discretion and convenience benefits. However, current plastic tampon applicators are made of injection molded materials such as polyolefins (e.g., polypropylenes or polyethylenes) and polyesters that are not biodegradable or renewable, as the use of biodegradable polymers in an injection molded part is problematic due to the difficulty involved with thermally processing such polymers and high cost. As such, consumers must dispose of tampon applicators in a separate waste receptacle, which results in a challenge for consumers to dispose of the applicators in a discrete and convenient manner. Furthermore, the soiled or used tampon applicator may also pose a biohazard or potential health hazard. As a result, although current plastic tampon applicators are not supposed to be flushed, some consumers may nevertheless attempt to flush the applicators in the toilet, which can lead to clogging of sewer pipes and municipal waste water treatment facilities. Attempts have been made to mold cold water-dispersible materials such as polyvinyl alcohol in order to alleviate these problems, but such attempts have not been successful. Instead, when using polyvinyl alcohol in tampon applicators, the materials must be solution processed so that they can be formed into a tampon applicator that has a thick enough wall, and such solution processing is a slow, costly, environmentally unsustainable process that necessitates high energy requirements. Further, although cardboard applicators have been developed, the cardboard must often be coated to decrease the coefficient of friction of the applicator to a comfortable level for consumers, and the coatings used are not environmentally friendly and add to the costs associated with forming the applicator.

As such, a need currently exists for a thermoplastic, water-dispersible composition that can be injection molded, where such composition can be successfully formed into a tampon applicator. A need also exists for a water-dispersible applicator that is comfortable to insert and that does not begin to break down upon insertion.

SUMMARY OF THE INVENTION

In accordance with one embodiment of the present invention, a flushable tampon applicator is disclosed. The tampon applicator includes an outer tube for housing a tampon and also includes an inner tube, at least a portion of which extends into the outer tube. The outer tube includes an outer, body-contacting surface such that the inner tube is moveable relative to the outer tube and configured to expel a tampon from the outer tube. At least one of the outer tube and the inner tube is a molded part. Further, at least one of the outer tube and the inner tube includes a thermoplastic composition. The thermoplastic composition includes from about 50 wt. % to about 98 wt. % of partially hydrolyzed polyvinyl alcohols. The partially hydrolyzed polyvinyl alcohols include a first polyvinyl alcohol and a second polyvinyl alcohol, where the viscosity of the first polyvinyl alcohol is less than the viscosity of the second polyvinyl alcohol. In addition, the weight percentage ratio of the first polyvinyl alcohol to the second polyvinyl alcohol ranges from about 1 to about 20. The thermoplastic composition also includes from about 2 wt. % to about 50 wt. % of a plasticizer.

In accordance with another embodiment of the present disclosure, a method for forming an injection molded part is disclosed. The method includes injection molding a pelletized, water-dispersible, thermoplastic composition into a mold cavity and shaping the thermoplastic composition into a molded part within the mold cavity. Meanwhile, the thermoplastic composition comprises from about 50 wt. % to about 98 wt % of partially hydrolyzed polyvinyl alcohols. Further, the partially hydrolyzed polyvinyl alcohols include a first polyvinyl alcohol and a second polyvinyl alcohol, where the viscosity of the first polyvinyl alcohol is less than the viscosity of the second polyvinyl alcohol. In addition, the weight percentage ratio of the first polyvinyl alcohol to the second polyvinyl alcohol ranges from about 1 to about 20. The thermoplastic composition also includes from about 2 wt. % to about 50 wt. % of a plasticizer and has a melt flow rate of from about 40 grams per 10 minutes to about 160 grams per 10 minutes when subjected to a load of 2160 grams at a temperature of 190° C. according to ASTM Test Method D1238-E.

In accordance with still another embodiment of the present disclosure, a water-dispersible, thermoplastic composition is disclosed. The thermoplastic composition includes from about 50 wt. % to about 98 wt. % of partially hydrolyzed polyvinyl alcohols. The partially hydrolyzed polyvinyl alcohols include a first polyvinyl alcohol and a second polyvinyl alcohol, where the weight percentage ratio of the first polyvinyl alcohol to the second polyvinyl alcohol ranges from about 1 to about 20. Additionally, the first polyvinyl alcohol has a viscosity ranging from about 1 centipoise to about 3.5 centipoise and the second polyvinyl alcohol has a viscosity ranging from about 3.5 centipoise to about 15 centipoise. The thermoplastic composition also includes from about 2 wt. % to about 50 wt. % of a plasticizer and has a melt flow rate of from about 40 grams per 10 minutes to about 160 grams per 10 minutes when subjected to a load of 2160 grams at a temperature of 190° C. according to ASTM Test Method D1238-E.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a thermoplastic composition that is water-sensitive (e.g., water-soluble, water-dispersible, etc.) in that it loses its integrity over time in the presence of water, yet also has a high enough melt flow index and a low enough melt viscosity such that it can be molded into an article such as a tampon applicator. For instance, the thermoplastic composition has a high enough melt flow index and a low enough melt viscosity such that it can be injected molded. The composition contains partially hydrolyzed polyvinyl alcohols and a plasticizer. The desired water-sensitive attributes and mechanical properties of the composition and the resulting molded articles, such as tampon applicators, may be achieved in the present invention by selectively controlling a variety of aspects of the composition, such as the nature of each of the components employed, the relative amount of each component, the ratio of the weight percentage of one component to the weight percentage of another component, the manner in which the composition is formed, and so forth.

Further, the tampon applicator of the present invention can include an outer tube and an inner tube, one or both of which can be formed from the thermoplastic, water-dispersible composition of the present invention such that the tampon applicator is flushable and can disintegrate in water. The outer tube houses a tampon, and the inner tube is used to engage the tampon contained in the outer tube. The outer tube can include an insertion tip which may also be formed from the thermoplastic, water-dispersible composition of the present invention. Because there is a possibility that the tampon applicator, and in particular, the outer tube, can become sticky when used due to the moist environment in which it is used, one or more components of the tampon applicator can be coated or layered with a less water-dispersible composition, such as polytetrafluoroethylene (PTFE) or high density polyethylene (HDPE). In some embodiments, only the body-contacting components of the tampon applicator, such as an outer surface of the outer tube and/or insertion tip, can include the additional coating or layer, which can be co-injection molded. In other embodiments, non-body contacting components, such as the inner tube, can also include the additional coating or layer.

In this regard, various embodiments of the present invention will now be described in more detail below.

I. Thermoplastic Composition Components

A. Polyvinyl Alcohol Polymer

The water-dispersible, thermoplastic composition includes one or more polymers containing a repeating unit having a functional hydroxyl group, such as polyvinyl alcohol ("PVOH"), copolymers of polyvinyl alcohol (e.g., ethylene vinyl alcohol copolymers, methyl methacrylate vinyl alcohol copolymers, etc.), etc. Vinyl alcohol polymers, for instance, have at least two or more vinyl alcohol units in the molecule and may be a homopolymer of vinyl alcohol, or a copolymer containing other monomer units. Vinyl alcohol homopolymers may be obtained by hydrolysis of a vinyl ester polymer, such as vinyl formate, vinyl acetate, vinyl propionate, etc. Vinyl alcohol copolymers may be obtained by hydrolysis of a copolymer of a vinyl ester with an olefin having 2 to 30 carbon atoms, such as ethylene, propylene, 1-butene, etc.; an unsaturated carboxylic acid having 3 to 30 carbon atoms, such as acrylic acid, methacrylic acid, crotonic acid, maleic acid, fumaric acid, etc., or an ester, salt, anhydride or amide thereof; an unsaturated nitrile having 3 to 30 carbon atoms, such as acrylonitrile, methacrylonitrile, etc.; a vinyl ether having 3 to 30 carbon atoms, such as methyl vinyl ether, ethyl vinyl ether, etc.; and so forth. The degree of hydrolysis may be selected to optimize solubility, etc., of the polymer. For example, the degree of hydrolysis may be from about 60 mole % to about 95 mole %, in some embodiments from about 80 mole % to about 90 mole %, and in some embodiments, from about 85 mole % to about 89 mole %, and in some embodiments from about 87 mole % to about 89 mole %. These partially hydrolyzed polyvinyl alcohols are cold water soluble. In contrast, the completely hydrolyzed or nearly hydrolyzed polyvinyl alcohols are not soluble in cold water.

At least two partially hydrolyzed polyvinyl alcohol polymers can be used in the thermoplastic, water-dispersible composition of the present invention. The at least two partially hydrolyzed polyvinyl alcohols can be present in an amount ranging from about 50 wt. % to about 98 wt. %, such as from about 55 wt. % to about 97 wt. %, such as from about 60 wt. % to about 96 wt. %, such as from about 65 wt. % to about 95 wt. % based on the total weight of the composition. The at least two partially hydrolyzed polyvinyl alcohols can be present in varying amounts based on the total weight of the composition. For instance, a low viscosity partially hydrolyzed polyvinyl alcohol can be combined with one or more high viscosity partially hydrolyzed polyvinyl alcohols. The low viscosity (e.g., low molecular weight) polyvinyl alcohol can result in a composition having a high melt flow rate while at the same time utilizing a lower level of plasticizer, which can prevent the migration or blooming of the plasticizer to the surface. On the other hand, utilizing a low viscosity partially hydrolyzed polyvinyl alcohol results in low elongation at break properties, which corresponds with a material that is brittle and not ductile. As such, one or more higher viscosity (higher molecular weight) partially hydrolyzed polyvinyl alcohols can be combined with the low viscosity partially hydrolyzed polyvinyl alcohol to provide for improved ductility, as evidenced by an increased percent elongation at break and lower modulus. However, more plasticizer is required to achieve a high enough melt flow rate for the higher viscosity partially hydrolyzed polyvinyl alcohols to become thermoplastic and injection moldable, so a careful balance must achieved to obtain the desired melt flow rate mechanical properties for an injection molded part without the use of too much plasticizer, which can migrate during processing and storage.

Generally, the ratio of the low viscosity partially hydrolyzed polyvinyl alcohol present in the composition (e.g., SELVOL™ 502) to the high viscosity partially hydrolyzed water-soluble polymer(s) present in the composition (e.g., SELVOL™ 203 and 205) can range from about 1 to about 20, such as from about 1.25 to about 15, such as from about 1.5 to about 10. By controlling the ratio of the low viscosity partially hydrolyzed water-soluble polymer to the high viscosity partially hydrolyzed water-soluble polymer(s) in this manner, a composition with a high enough melt flow rate such that it can be injection molded can be achieved, which can be attributed to the low viscosity partially hydrolyzed polyvinyl alcohol, while at the same time not sacrificing the mechanical properties of the resulting injection molded part, which can be attributed to the high viscosity partially hydrolyzed polyvinyl alcohol(s). For instance, the high viscosity partially hydrolyzed polyvinyl alcohol(s) can contribute to the ductility (lower modulus, higher elongation) of the composition to counteract any brittleness (high modulus, lower elongation) that can be attributed at least in part to the low viscosity partially hydrolyzed polyvinyl alcohol, where the low viscosity partially hydrolyzed polyvinyl alcohol can increase the melt flow rate to a high enough level so that the resulting composition can be injection molded. By using the low viscosity partially hydrolyzed polyvinyl alcohol in the thermoplastic composition of the present invention, a low level of plasticizer is needed, which avoids issues related to plasticizer migration or blooming. However, it has also been discovered that by selectively controlling the types and ratios of partially hydrolyzed polyvinyl alcohols utilized, a higher melt flow rate can be achieved even when using high viscosity partially hydrolyzed polyvinyl alcohols, which provide for the enhanced ductility of articles molded from the thermoplastic composition of the present invention.

The low viscosity partially hydrolyzed polyvinyl alcohol(s) can have a viscosity ranging from about 1 centipoise (cps) to about 3.5 cps, such as from about 2 cps to about 3.45 cps, such as from about 3 cps to about 3.4 cps. Meanwhile the high viscosity partially hydrolyzed polyvinyl alcohol(s) can have a viscosity ranging from about 3.5 cps to about 15 cps, such as from about 3.75 cps to about 12 cps, such as from about 4 cps to about 10 cps. Further, in some embodiments, the low viscosity partially hydrolyzed polyvinyl alcohol can be present in an amount ranging from about 20 wt. % to about 80 wt. %, such as from about 35 wt. % to about 75 wt. %, such as from about 40 wt. % to about 70 wt. % based on the total weight of the composition. Meanwhile, the one or more high viscosity partially hydrolyzed polyvinyl alcohols can be present in an amount ranging from about 1 wt. % to about 50 wt. %, such as from about 2.5 wt. % to about 40 wt. %, such as from about 5 wt. % to about 30 wt. % based on the total weight of the polymer composition. Further, when two or more of the high viscosity partially hydrolyzed polyvinyl alcohol polymers is present, the weight percentage ratio of the high viscosity partially hydrolyzed polyvinyl alcohol polymer having the lower viscosity of the two high viscosity partially hydrolyzed polyvinyl alcohol polymers to the high viscosity partially hydrolyzed polyvinyl alcohol polymer having the higher viscosity of the two high viscosity partially hydrolyzed polyvinyl alcohol polymers can range from about 1 to about 10, such as from about 1.25 to about 9, such as from about 1.5 to about 8.

Examples of suitable partially hydrolyzed polyvinyl alcohol polymers are available under the designation SELVOL™ 203, 205, 502, 504, 508, 513, 518, 523, 530, or 540 from Sekisui Specialty Chemicals America, LLC of Dallas, Tex. For instance, SELVOL™ 203 has a percent hydrolysis of 87% to 89% and a viscosity of 3.5 to 4.5 centipoise (cps) as determined from a 4% solids aqueous solution at 20° C. SELVOL™ 205 has a percent hydrolysis of 87% to 89% and a viscosity of 5.2 to 6.2 centipoise (cps) as determined using a 4% solids aqueous solution at 20° C. SELVOL™ 502 has a percent hydrolysis of 87% to 89% and a viscosity of 3.0 to 3.7 centipoise (cps) as determined as determined using a 4% solids aqueous solution at 20° C. SELVOL™ 504 has a percent hydrolysis of 87% to 89% and a viscosity of 4.0 to 5.0 centipoise (cps) as determined from a 4% solids aqueous solution at 20° C. SELVOL™ 508 has a percent hydrolysis of 87% to 89% and a viscosity of 7.0 to 10.0 centipoise (cps) as determined as determined from a 4% solids aqueous solution at 20° C. Other suitable partially hydrolyzed polyvinyl alcohol polymers are available under the designation ELVANOL™ 50-14, 50-26, 50-42, 51-03, 51-04, 51-05, 51-08, and 52-22 from DuPont as well as the SELVOL™ line of polyvinyl alcohols available from Celanese Corp. For instance, ELVANOL™ 51-05 has a percent hydrolysis of 87% to 89% and a viscosity of 5.0 to 6.0 centipoise (cps) as determined from a 4% solids aqueous solution at 20° C. In the present invention, the polyvinyl alcohols characterized as having a low viscosity include SELVOL™ 502 (3.0 to 3.7 cps), where the midpoint or average viscosity for the low viscosity polyvinyl alcohol is generally less than about 3.35 cps, as determined by averaging the minimum and maximum viscosities provided for commercially available partially hydrolyzed polyvinyl alcohols. Meanwhile, the polyvinyl alcohols characterized as having a high viscosity include SELVOL™ 203 (3.5 to 4.5 cps), SELVOL 504™ (4.0-5.0 cps), ELVANOL™ 51-05 (5.0 to 6.0 cps), SELVOL™ 205 (5.2 to 6.2 cps), and SELVOL™ 508 (7.0-10.0 cps), where the midpoint or average viscosity for the high viscosity polyvinyl alcohol polymers is at least about 4.0 cps, as determined by averaging the minimum and maximum viscosities provided for commercially available partially hydrolyzed polyvinyl alcohols.

B. Plasticizer

A plasticizer is also employed in the water-dispersible, thermoplastic composition to help render the water-soluble polymer thermoplastic and thus suitable for extrusion into pellets and subsequent injection molding. Suitable plasticizers may include, for instance, polyhydric alcohol plasticizers, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), polyethylene glycols, etc. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic acids may also be used, such as ethylene acrylic acid, ethylene maleic acid, butadiene acrylic acid, butadiene maleic acid, propylene acrylic acid, propylene maleic acid, and other hydrocarbon based acids. A low molecular weight plasticizer is preferred, such as less than about 20,000 g/mol, preferably less than about 5,000 g/mol and more preferably less than about 1,000 g/mol.

The plasticizer may be incorporated into the composition of the present invention using any of a variety of known techniques. For example, the water-soluble polymers may be "pre-plasticized" prior to incorporation into the composition. Alternatively, one or more of the components may be plasticized at the same time as they are blended together. Regardless, batch and/or continuous melt blending techniques may be employed to blend the components. For example, a mixer/kneader, Banbury mixer, Farrel continuous mixer, single-screw extruder, twin-screw extruder, roll mill, etc., may be utilized. One particularly suitable melt-blending device is a co-rotating, twin-screw extruder (e.g., USALAB twin-screw extruder available from Thermo Electron Corporation of Stone, England or an extruder available from Werner-Pfleiderer from Ramsey, N.J.). Such extruders may include feeding and venting ports and provide high intensity distributive and dispersive mixing. For example, the water-soluble polymers may be initially fed to a feeding port of the twin-screw extruder to form a composition. Thereafter, a plasticizer may be injected into the composition. Alternatively, the composition may be simultaneously fed to the feed throat of the extruder or separately at a different point along the length of the extruder. Melt blending may occur at any of a variety of temperatures, such as from about 30° C. to about 240° C., in some embodiments, from about 40° C. to about 200° C., and in some embodiments, from about 50° C. to about 180° C.

Plasticizers can be present in the water-dispersible, thermoplastic composition in an amount ranging from about 2 wt. % to about 50 wt %, such as from about 3 wt. % to about 45 wt. %, such as from about 5 wt % to about 40 wt. %, based on the total weight of the composition. In some embodiments, the plasticizer can be present in an amount of 10 wt % or greater, such as from about 10 wt. % to about 35 wt. %, such as from about 10 wt % to about 30 wt. %, such as from about 10 wt % to about 25 wt % based on the total weight of the composition.

C. Fillers

Although the combination of the two or more partially hydrolyzed polyvinyl alcohols and plasticizer may achieve the desired water-solubility required for a water-dispersible, thermoplastic composition, it may still often be difficult to achieve a precise set of mechanical properties as desired for injected molded articles. In this regard, the composition can also contain one or more fillers. Due to its rigid nature, the amount of the filler may be readily adjusted to fine tune the composition to the desired degree of ductility (e.g., peak elongation) and stiffness (e.g., modulus of elasticity).

The filler of the present invention may include particles having any desired size, such as those having an average size of from about 0.5 to about 10 micrometers, in some embodiments, from about 1 to about 8 micrometers, and in some embodiments, from about 2 to about 6 micrometers. Suitable particles for use as a filler may include inorganic oxides, such as calcium carbonate, kaolin clay, silica, alumina, barium carbonate, sodium carbonate, titanium dioxide, zeolites, magnesium carbonate, calcium oxide, magnesium oxide, aluminum hydroxide, talc, etc.; sulfates, such as barium sulfate, magnesium sulfate, aluminum sulfate, etc.; cellulose-type powders (e.g., pulp powder, wood powder, etc.); carbon; cyclodextrins; synthetic polymers (e.g., polystyrene), and so forth. Still other suitable particles are described in U.S. Pat. Nos. 6,015,764 and 6,111,163 to McCormack, et al., U.S. Pat. No. 5,932,497 to Morman, et al., U.S. Pat. No. 5,695,868 to McCormack, U.S. Pat. No. 5,855,999 to McCormack et al., U.S. Pat. No. 5,997,981 to McCormack et al., and U.S. Pat. No. 6,461,457 to Taylor, et al., which are incorporated herein in their entirety by reference thereto for all purposes.

In one particular embodiment, the filler includes particles formed from calcium carbonate. If desired, calcium carbonate particles may be employed that have a purity of at least about 95 wt. %, in some embodiments at least about 98 wt. %, and in some embodiments, at least about 99 wt. %. Such high purity calcium carbonates are generally fine, soft, and round, and thus provide a more controlled and narrow particle size for improving the properties of the composition. An example of such a high purity calcium carbonate is Caribbean micritic calcium carbonate, which is mined from soft and friable, finely divided, chalk-like marine sedimentary deposits frequently occurring as surface deposits in the Caribbean (e.g., Jamaica). Such calcium carbonates typically have an average particle size of about 10 micrometers or less, and desirably about 6 micrometers or less. Other examples of Caribbean micritic calcium carbonates are described in U.S. Pat. No. 5,102,465 to Lamond, which is incorporated herein in its entirety by reference thereto for all purposes. Such calcium carbonates may be wet or dry ground, and classified into a narrow particle size distribution with round or spherical-shaped particles. One particularly suitable micritic calcium carbonate is available from Specialty Minerals under the designation "MD1517."

Although not required, the filler may optionally be coated with a modifier (e.g., fatty acid, such as stearic acid or behenic acid) to facilitate the free flow of the particles in bulk and their ease of dispersion into the composition. The filler may be pre-compounded with such additives before mixing with the other components of the composition, or the additives may be compounded with the other components of the composition and fillers at the melt-blending step.

When present, the fillers can be present in an amount ranging from about 0.5 wt. % to about 35 wt %, such as from about 1 wt. % to about 30 wt. %, such as from about 2 wt. % to about 25 wt. %, such as from about 3 wt. % to about 20 wt. % based on the total weight of the water-dispersible, thermoplastic composition.

D. Coloring Agents

In addition, the water-dispersible, thermoplastic composition can contain one or more coloring agents (e.g., pigment or dye). Typically, a pigment refers to a colorant based on inorganic or organic particles which do not dissolve in water or solvents. Usually pigments form an emulsion or a suspension in water. On the other hand, a dye generally refers to a colorant that is soluble in water or solvents.

The pigment or dye can be present in an amount effective to be visible once the composition is formed into an injection molded article so that articles from the composition can have an aesthetically pleasing appearance to the user. Suitable organic pigments, include dairylide yellow AAOT (for example, Pigment Yellow 14 Cl No. 21 095), dairylide yellow AAOA (for example, Pigment Yellow 12 Cl No. 21090), Hansa Yellow, Cl Pigment Yellow 74, Phthalocyanine Blue (for example, Pigment Blue 15), lithol red (for example, Pigment Red 52:1 Cl No. 15860:1), toluidine red (for example, Pigment Red 22 Cl No. 12315), dioxazine violet (for example, Pigment Violet 23 Cl No, 51319), phthalocyanine green (for example, Pigment Green 7 Cl No. 74260), phthalocyanine blue (for example, Pigment Blue 15 Cl No. 74160), naphthoic acid red (for example, Pigment Red 48:2 Cl No. 15865:2). Inorganic pigments include titanium dioxide (for example, Pigment White 6 Cl No. 77891), iron oxides (for example, red, yellow, and brown), chromium oxide (for example, green), ferric ammonium ferrocyanide (for example, blue), and the like.

Suitable dyes that may be used include, for instance, acid dyes, and sulfonated dyes including direct dyes. Other suitable dyes include azo dyes (e.g., Solvent Yellow 14, Dispersed Yellow 23, and Metanil Yellow), anthraquinone dyes (e.g., Solvent Red 111. Dispersed Violet 1, Solvent Blue 56, and Solvent Orange 3), xanthene dyes (e.g., Solvent Green 4, Acid Red 52, Basic Red 1, and Solvent Orange 63), azine dyes, and the like.

When present, the coloring agents can be present in the water-dispersible, thermoplastic composition in an amount ranging from about 0.5 wt. % to about 20 wt. %, such as from about 1 wt. % to about 15 wt. %, such as from about 1.5 wt. % to about 12.5 wt %, such as from about 2 wt. % to about 10 wt. % based on the total weight of the water-dispersible, thermoplastic composition.

E. Other Optional Components

In addition to the components noted above, other additives may also be incorporated into the composition of the present invention, such as dispersion aids, melt stabilizers, processing stabilizers, heat stabilizers, light stabilizers, antioxidants, heat aging stabilizers, whitening agents, antiblocking agents, bonding agents, lubricants, etc. Dispersion aids, for instance, may also be employed to help create a uniform dispersion of the polyvinyl alcohol/plasticizer mixture and retard or prevent separation into constituent phases. Likewise, the dispersion aids may also improve the water dispersibility of the composition. Although any dispersion aid may generally be employed in the present invention, surfactants having a certain hydrophilic/lipophilic balance ("HLB") may improve the long-term stability of the composition. The HLB index is well known in the art and is a scale that measures the balance between the hydrophilic and lipophilic solution tendencies of a compound. The HLB scale ranges from 1 to approximately 50, with the lower numbers representing highly lipophilic tendencies and the higher numbers representing highly hydrophilic tendencies. In some embodiments of the present invention, the HLB value of the surfactants is from about 1 to about 20, in some embodiments from about 1 to about 15 and in some embodiments, from about 2 to about 10. If desired, two or more surfactants may be employed that have HLB values either below or above the desired value, but together have an average HLB value within the desired range.

One particularly suitable class of surfactants for use in the present invention are nonionic surfactants, which typically have a hydrophobic base (e.g., long chain alkyl group or an alkylated aryl group) and a hydrophilic chain (e.g., chain containing ethoxy and/or propoxy moieties). For instance, some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. In one particular embodiment, the nonionic surfactant may be a fatty acid ester, such as a sucrose fatty acid ester, glycerol fatty acid ester, propylene glycol fatty acid ester, sorbitan fatty acid ester, pentaerythritol fatty acid ester, sorbitol fatty acid ester, and so forth. The fatty acid used to form such esters may be saturated or unsaturated, substituted or unsubstituted, and may contain from 6 to 22 carbon atoms, in some embodiments from 8 to 18 carbon atoms, and in some embodiments, from 12 to 14 carbon atoms. In one particular embodiment, mono- and di-glycerides of fatty acids may be employed in the present invention.

When employed, the dispersion aid(s) typically constitute from about 0.01 wt. % to about 15 wt. %, such as from about 0.1 wt. % to about 10 wt. %, such as from about 0.5 wt. % to about 5 wt. %, such as from about 1 wt, % to about 3 wt. % based on the total weight of the water-dispersible, thermoplastic composition.

II. Molded Parts

A molded part can be formed from the water-dispersible, thermoplastic composition of the present disclosure using any of a variety of techniques known in the art, such as extrusion blow molding, injection molding, rotational molding, compression molding, etc., as well as combinations of the foregoing. For instance, the present inventors have found that through the selective control of the specific components of the composition and their weight percentage ratios, a thermoplastic water-dispersible composition having a high enough melt flow index and a low enough viscosity can first be melt extruded into pellets as a homogeneous material, after which the extruded pellets can be used in injection molding applications. Further, articles molded from the extruded pellets can have the desired mechanical properties despite being water-dispersible. Generally, the melt flow index of the water-dispersible, thermoplastic composition can range from about 40 grams per 10 minutes to about 200 grams per 10 minutes, in some embodiments from about 45 grams per 10 minutes to about 180 grams per 10 minutes, and in some embodiments, from about 50 grams per 10 minutes to about 160 grams per 10 minutes. The melt flow index is the weight of a polymer (in grams) that may be forced through an extrusion rheometer orifice (0.0825-inch diameter) when subjected to a load of 2160 grams in 10 minutes at a certain temperature (e.g., 190° C.), measured in accordance with ASTM Test Method D1238-E. The melt flow index corresponds with a viscosity that is low enough so that the composition of the present invention can be extruded and also pushed through an orifice into a mold during injection molding, for example.

Regardless of the molding process selected, the thermoplastic composition may be used alone to form the molded part, or in combination with other polymeric components to form a molded part. For example, in some embodiments, other polymer(s) can be injected or transferred into a mold during a co-injection molding process to form a water-insoluble skin layer around a water-dispersible core layer of the composition of the present invention. Tie layers between the core layer and skin layer may also be formed. Examples of machines suitable for co-injection, sandwich, or two-component molding include machines produced by Presma Corp., Northeast Mold & Plastics, Inc. Although not required, the core of such a part is typically formed from the thermoplastic composition of the present invention and the skin layer is typically formed from a different material (e.g., a wax, a silicon (e.g., polysiloxane), polytetrafluoroethylene, a polyolefin (e.g., polyethylene), a polyester, a polyamide, a thermoplastic elastomer (e.g., polyurethane or a polyolefin-based elastomer), or a combination thereof) that enhances the surface properties on the molded part. For instance, when the molded part is a tampon applicator, the skin layer can have a reduced coefficient of friction to provide more comfort to the user. In addition, the skin layer can have a lower level of water sensitivity such that the applicator is less likely to begin disintegrating during use.

Further, in other embodiments, the skin layer can be a coating that is applied to an injection molded part containing the thermoplastic composition of the present invention. Meanwhile, in other embodiments, a water-insoluble polymer can be blended with one or more water-soluble polymers (e.g., one or more partially hydrolyzed polyvinyl alcohols), then melt extruded to form a macroscopically homogeneous mixture, while microscopically, two or more phases exist within the extrudate, which can then be injection molded to form a flushable applicator.

Figure 1:
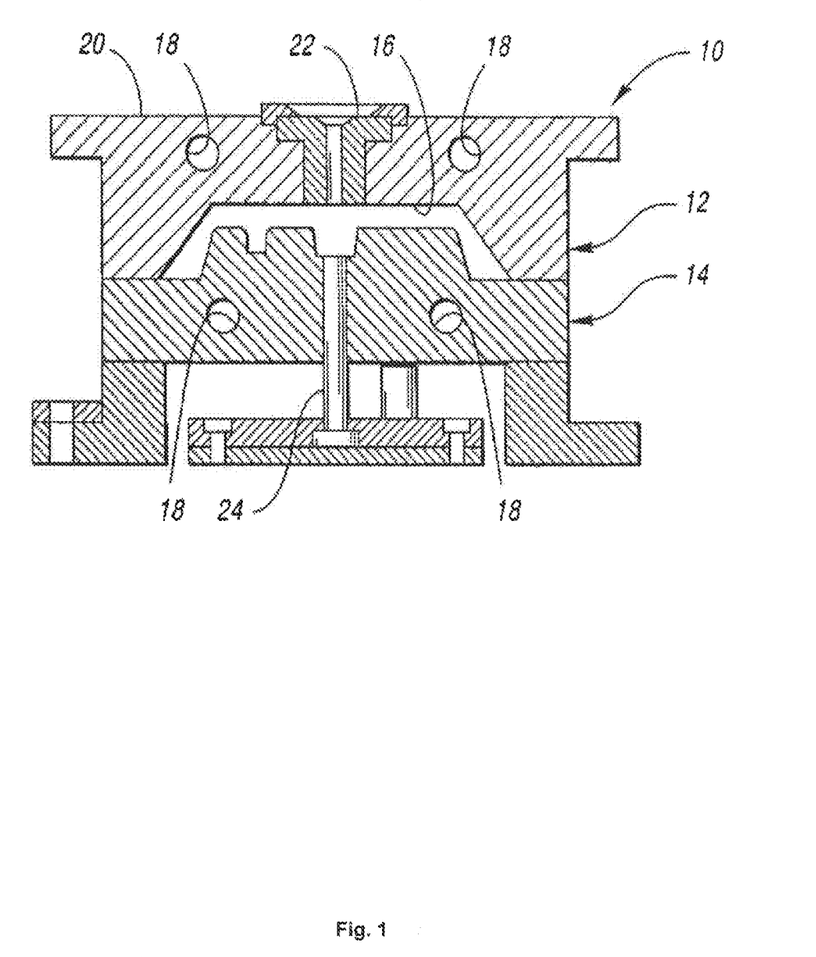
FIG. 1 is a schematic illustration of one embodiment of an injection molding apparatus for use in the present invention.

Referring to FIG. 1, for example, one particular embodiment of a single-component injection molding apparatus or tool 10 that may be employed in the present invention is shown in more detail. In this embodiment, the apparatus 10 includes a first mold base 12 and a second mold base 14, which together define an article or component-defining mold cavity 16. Each of the mold bases 12 and 14 includes one or more cooling lines 18 through which a cooling liquid such as water flows to cool the apparatus 10 during use. The molding apparatus 10 also includes a resin flow path that extends from an outer exterior surface 20 of the first mold half 12 through a sprue 22 to the mold cavity 16. The resin flow path may also include a runner and a gate, both of which are not shown for purposes of simplicity. The molding apparatus 10 also includes one or more ejector pins 24 slidably secured within the second mold half 14 that helps to define the mold cavity 16 in the closed position of the apparatus 10, as indicated in FIG. 1. The ejector pin 24 operates in a well-known fashion to remove a molded part from the cavity 16 in the open position of the molding apparatus 10.

The thermoplastic composition may be directly injected into the molding apparatus 10 using techniques known in the art. For example, the molding material may be supplied in the form of pellets to a feed hopper attached to a barrel that contains a rotating screw (not shown). As the screw rotates, the pellets are moved forward and undergo extreme pressure and friction, which generates heat to melt the pellets. Electric heater bands (not shown) attached to the outside of the barrel may also assist in the heating and temperature control during the melting process. For example, the bands may be heated to a temperature of from about 200° C. to about 260° C., in some embodiments from about 230° C. to about 255° C., and in some embodiments, from about 240° C. to about 250° C. Upon entering the molding cavity 16, the molding material is solidified by the cooling liquid flowing through the lines 18. The cooling liquid may, for example, be at a temperature (the "molding temperature") of from about 5° C. to about 50° C., in some embodiments from about 10° C. to about 40° C., and in some embodiments, from about 15° C. to about 30° C.

The molded parts may have a variety of different sizes and configurations. For instance, the molded parts may be used to form various parts used in personal care applications. For instance, in one particular embodiment, the molded part is used to form a tampon applicator that is water-dispersible. The molded part can disintegrate in tap water in less than about 18 hours, such as less than about 12 hours, such as less than about 4 hours. In some embodiments, the molded part can disintegrate in tap water in less than about 3 hours, such as less than about 2 hours, such as in from about 5 minutes to about 100 minutes. Further, due to the specific combination of partially hydrolyzed polyvinyl alcohol polymers, the molded part can disintegrate in cool tap water having a temperature less than about 25° C., such as from about 5° C. to about 20° C., such as from about 10° C.° to about 15° C.

Further, molded parts containing the water-dispersible, thermoplastic composition of the present invention can have a peak stress of from about 2 MPa to about 50 MPa, such as from about 5 MPa to about 40 MPa, such as from about 10 MPa to about 30 MPa; an elongation at break of from about 40% to about 200%, such as from about 45% to about 175%, such as from about 50% to about 150%; and a modulus of from about 100 MPa to about 2000 MPa, such as from about 125 MPa to about 1900 MPa, such as from about 150 MPa to about 1800 MPa.

The molded parts discussed above may have a variety of different sizes and configurations. For instance, the molded parts may be used to form various parts used in personal care applications. For instance, in one particular embodiment, the molded part is used to form a tampon applicator that is water-dispersible.

Figure 2:
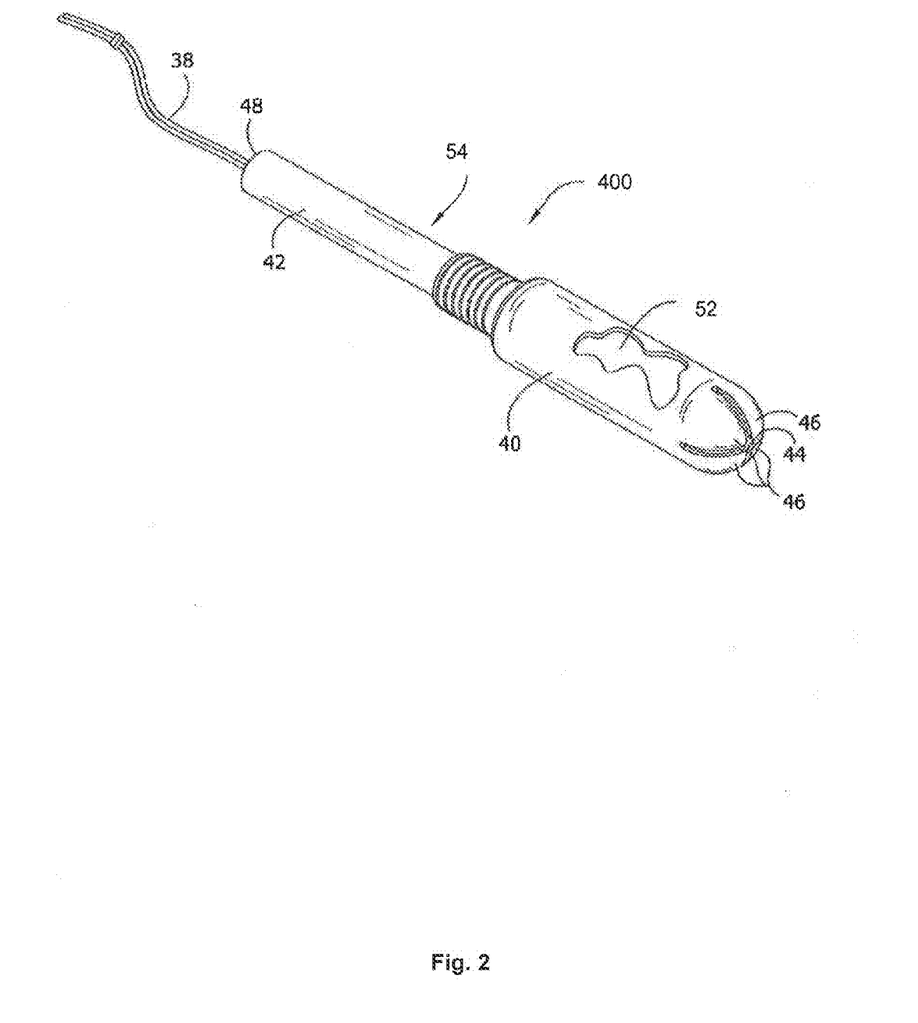
FIG. 2 is a perspective view of one embodiment of a water-dispersible tampon applicator as contemplated by the present invention.

As illustrated in the tampon assembly 400 of FIG. 2, the tampon applicator 54 comprises an outer tube 40 and an inner tube 42. The outer tube 40 is sized and shaped to house a tampon 52. A portion of the outer tube 40 is partially broken away in FIG. 2 to illustrate the tampon 52. In the illustrated embodiment, the outer tube 40 has a substantially smooth exterior surface, which facilitates insertion of the tampon applicator 54 without subjecting the internal tissues to abrasion. The outer tube 40 may be coated to give it a high slip characteristic. The illustrated outer tube 40 is a straight, elongated cylindrical tube. It is understood however that the applicator 54 could have different shapes and sizes than those illustrated and described herein.

Extending outwardly from the outer tube is an insertion tip 44. The insertion tip 44, which is formed as one-piece with the outer tube 40, may be dome-shaped to facilitate insertion of the outer tube into a woman's vagina in a comfortable manner. The illustrated insertion tip 44 is made of a thin, flexible material and has a plurality of soft, flexible petals 46 that are arranged to form the dome-shape. The petals 46 are capable of radially flexing (i.e., bending outward) to provide an enlarged opening through which the tampon 52 can exit when it is pushed forward by the inner tube 42. It is to be understood, however, that the outer tube 40 may be formed without the insertion tip 44. Without the insertion tip, the outer tube includes an opened end (not shown) through which the tampon 52 can exit when it is pushed forward by the inner tube.

The inner tube 42 is an elongate cylinder that is used to engage the tampon 52 contained in the outer tube 40. A free end 48 of the inner tube 42 is configured so that the user can move the inner tube with respect to the outer tube 40. In other words, the free end 48 functions as a grip for the forefinger of the user. The inner tube 42 is used to push the tampon 52 out of the outer tube 40 and into the woman's vagina by telescopically moving into the outer tube. As the inner tube 42 is pushed into the outer tube 40 by the user, the tampon 52 is forced forward against the insertion tip 44. The contact by the tampon 52 causes the petals 46 of the insertion tip 44 to radially open to a diameter sufficient to allow the tampon to exit the outer tube 40 and into the woman's vagina. With the tampon 52 properly positioned in the woman's vagina, the tampon applicator 54 is withdrawn. In a used configuration of the tampon applicator 54, the inner tube 42 is received in the outer tube 40.

The inner tube 42, the outer tube 40, and the insertion tip 44 can be formed from one or more layers, where one layer includes the water-dispersible, thermoplastic composition of the present invention. Further, to prevent the applicator 54 from prematurely disintegrating due to moisture during use and/or to reduce the coefficient of friction of the applicator 54 to make it more comfortable for the user, it can be coated with a water-insoluble material that also has a low coefficient of friction to enhance comfort and prevent disintegration during insertion of the applicator 54. The structure of the tampon applicator described above is conventional and known to those skilled in the art, and is described, for instance, in U.S. Pat. No. 8,317,765 to Loyd, et al., which is incorporated herein in its entirety by reference thereto for all purposes. Other tampon applicator structures that can be formed from the thermoplastic composition of the present invention are described, for instance, in U.S. Pat. No. 4,921,474 to Suzuki, et al. and U.S. Pat. No. 5,389,068 to Keck, as well as U.S. Patent Application Publication Nos. 2010/0016780 to VanDenBogart, et al, and 2012/0204410 to Matalish, et al., which are incorporated herein in their entirety by reference thereto for all purposes.

Figure 3:
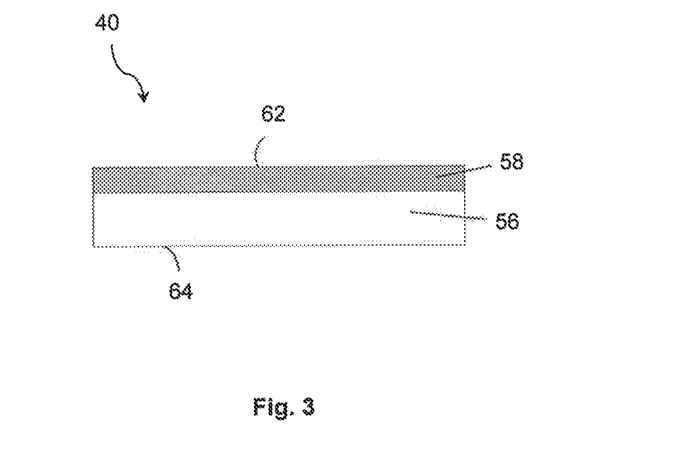
FIG. 3 is a cross-sectional view of one embodiment of a component of the tampon applicator of the present invention.

A cross-section of an outer tube 40 of tampon applicator 54, where the outer tube includes two layers, is shown in FIG. 3. The outer tube 40 can include an inner layer 56 having a tampon-facing surface 64 and an outer layer 58 having a body-contacting surface 62. The inner layer 56 can be formed from the water-dispersible, thermoplastic composition of the present invention, while the outer layer 58 can be formed from a water-insoluble material to prevent the tampon applicator from becoming sticky upon use and introduction to a moist environment and to provide a smooth surface for insertion. For instance, the outer layer 58 can be a layer or coating a wax, a silicon (e.g., polysiloxane), polytetrafluoroethylene, a polyolefin (e.g., polyethylene), a polyester, a polyamide, a thermoplastic elastomer (e.g., polyurethane or a polyolefin-based elastomer), or a combination thereof. It is also to be understood that while described above as a coating, the outer layer 58 can be an injection molded layer that can be formed prior to injecting the composition used to form the water-dispersible, inner layer 56.

The ratio of the weight percentage of the two layers can be selectively controlled to optimize the water-dispersibility of the tampon applicator, while at the same time not sacrificing the mechanical and physical properties required during use such that the applicator is stable when in contact with body fluids. Thus, the ratio of the weight percentage of the outer, body-contacting layer to the weight percentage of the inner, tampon facing layer of the tampon applicator can be from about 0.005 to about 1, such as from about 0.0075 to about 0.75, such as from about 0.01 to about 0.5. For example, the applicator can comprise from about 1 wt. % to about 50 wt. % of the outer, water insoluble layer, such as from about 5 wt. % to about 40 wt. %, such as from about 10 wt. % to about 30 wt. %. On the other hand, the applicator can comprise from about 50 wt. % to about 99 wt. % of the inner, water-dispersible layer, such as from about 60 wt. % to about 95 wt. %, such as from about 70 wt. % to about 90 wt. %.

Figure 4:
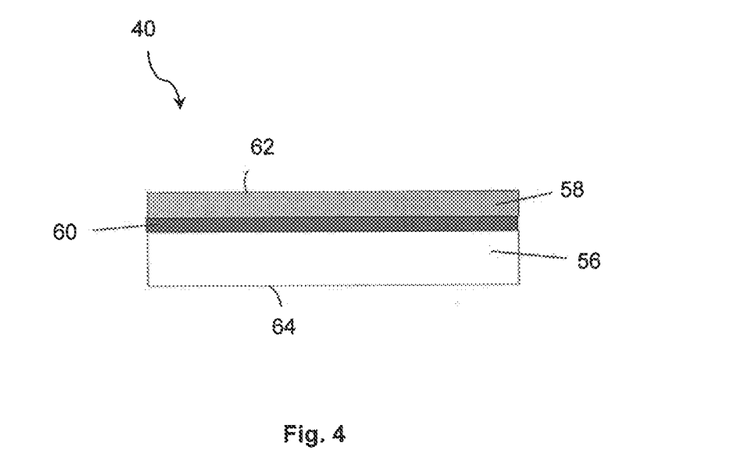
FIG. 4 is a cross-sectional view of another embodiment of a component of the tampon applicator of the present invention.

Meanwhile, FIG. 4 shows a cross section of an outer tube 40 of a tampon applicator 54, where the outer tube includes three layers. As in FIG. 3, the outer tube 40 can include an inner layer 56 having a tampon facing surface 64 and an outer layer 58 having a body facing surface 62. The inner layer 56 can be formed from the water-dispersible, thermoplastic composition of the present invention, while the outer layer 58 can be formed from a water-insoluble material to prevent the tampon applicator from becoming sticky upon use. For instance, the outer layer 58 can be a layer or coating of a wax, a silicon (e.g., polysiloxane), polytetrafluoroethylene, a polyolefin (e.g., polyethylene), a polyester, a polyamide, a thermoplastic elastomer (e.g., polyurethane or a polyolefin-based elastomer), or a combination thereof. Further, a tie layer 60 between the inner layer 56 and the outer layer 58 can improve the adhesion between the inner layer 56 and the outer layer 58. This layer can be an adhesive material which bonds the outer layer 58 and the inner layer 56. Alternatively, the tie layer can be a block copolymer or a graft copolymer, for example, such copolymers may be the outer layer polymer grafted with a polar vinyl monomer (i.e., polyethylene grafted with maleic anhydride or hydroxyethyl methacrylate if the outer layer material is polyethylene, the graft copolymer has good adhesion with both of the layers.

Although FIGS. 3 and 4 only show cross-sections of an outer tube 40, it is to be understood that other components of the tampon applicator 54, such as the insertion tip 44 and/or the inner tube 42, particularly components that contact the body, can also be formed from the multilayered articles illustrated in FIGS. 3 and 4, to prevent the components from becoming sticky during use, which can be uncomfortable for the user.

The present invention may be better understood with reference to the following example.

Test Methods

Melt Flow Rate

The melt flow rate ("MFR") is the weight of a polymer (in grams) forced through an extrusion rheometer orifice (0.0825-inch diameter) when subjected to a load of 2160 grams in 10 minutes, typically at 190° C. or 230° C. Unless otherwise indicated, melt flow rate is measured in accordance with ASTM Test Method D1239 with a Tinius Olsen Extrusion Plastometer. It should be noted that the melt flow rate measured at 190° C. may be referred to as the melt flow index (MFI), while those measured at other temperatures are called melt flow rates (MFR).

Tensile Properties

Tensile properties were determined by following ASTM D638-10 guidelines. ASTM D638-10 Type V injection molded test specimens were pulled via a MTS Mold 810 tensile frame with a 3,300 pound load cell. Five specimens were pulled from each example. The average values for peak stress (tensile strength), elongation at break, and modulus were reported. The maximum elongation that could be determined was 127% based on the tensile frame utilized, and the elongation was actually higher in the samples having 127% elongation readings.

Slosh Box Water Disintegration Test

In the slosh box water disintegration test, rather than placing samples in still water that did not circulate, the samples were placed in 1500 milliliters of tap water pre-cooled to 15° C. Injection molded samples weighing between 4 grams and 5 grams and having a thickness of 0.05 inches were added to the pre-chilled water and rocked back and forth at a rate of 26 rotations per minute (rpm). The length of time until the samples were totally dispersed was recorded, with a target disintegration time of less than 180 minutes.

EXAMPLE

Various polyvinyl alcohol compositions were formed as follows in an attempt to convert each of the samples into a melt extrudable, thermoplastic material that was also water dispersible. The resins were produced on the ZSK-30 co-rotating twin screw extruder with a resin compounding screw design. The resins were produced at a rate of 20 pounds per hour over a temperature range between 90° C. and 190° C. For the samples shown in Table 1, resins were produced at a rate of 20 pounds per hour. As indicated below in Table 1, one or more polyvinyl alcohols (SELVOL™ 502, 203, and/or 205) were dry blended prior to feeding into the main feed section of the twin screw extruder. SCCC 49487 colorant was fed using a separate feeder, also into the main feed section. Glycerin was injected into the polymer melt followed by calcium carbonate in later sections of the extruder. The various samples were extruded into homogeneous pellets, and the components of the samples produced are shown below in Table 1. The various samples were extruded into homogeneous pellets, and the components of the samples produced are shown below in Table 1. Meanwhile, the extrusion conditions are set forth below in Table 2. Further, the melt flow index, mechanical properties, and water disintegration times for injection molded samples produced from the extruded pellets containing the thermoplastic composition of the present invention, determined by the methods discussed above, are shown in Table 3.

TABLE 1

Sample Components

| Sample | SELVOL™ 502 (wt. %) | SELVOL™ 203 (wt. %) | SELVOL™ 205 (wt. %) | Glycerin (wt. %) | CaCO$_3$ (wt. %) | Colorant (wt. %) |
|---|---|---|---|---|---|---|
| 1  | 95 | —  | —  | 5  | —  | —  |
| 2  | 80 | —  | —  | 5  | 15 | —  |
| 3  | 40 | —  | 40 | 5  | 15 | —  |
| 4  | —  | —  | 71 | 14 | 15 | —  |
| 5  | 78 | —  | —  | 5  | 15 | 2  |
| 6  | 76 | —  | —  | 7  | 15 | 2  |
| 7  | 74 | —  | —  | 9  | 15 | 2  |
| 8  | —  | 74 | —  | 9  | 15 | 2  |
| 9  | —  | 72 | —  | 11 | 15 | 2  |
| 10 | —  | 70 | —  | 13 | 15 | 2  |
| 11 | —  | —  | 70 | 13 | 15 | 2  |
| 12 | —  | —  | 68 | 15 | 15 | 2  |
| 13 | —  | —  | 63 | 20 | 15 | 2  |
| 14 | 68 | —  | —  | 15 | 15 | 2  |
| 15 | 61 | 7  | —  | 15 | 15 | 2  |
| 16 | 66 | 7  | —  | 10 | 15 | 2  |
| 17 | 51 | 22 | —  | 10 | 15 | 2  |
| 18 | 48 | 20 | —  | 15 | 15 | 2  |
| 19 | 72 | —  | —  | 11 | 15 | 2  |
| 20 | 70 | —  | —  | 13 | 15 | 2  |
| 21 | 41 | 17 | 10 | 15 | 15 | 2  |
| 22 | 46 | 19 | 3  | 15 | 15 | 2  |

TABLE 2

Extrusion Conditions for Making Thermoplastic Water-Soluble Compositions

| Sample | Extruder Speed (rpm) | Extruder Temperature Profile (° C.) | | | | | | | Melting Temperature (° C.) | Melt Pressure (psi) | Torque (%) |
| | | $T_1$ | $T_2$ | $T_3$ | $T_4$ | $T_5$ | $T_6$ | $T_7$ | | | |
|---|---|---|---|---|---|---|---|---|---|---|---|
| 1  | 160 | 108 | 142 | 150 | 170 | 170 | 169 | 165 | 181 | 130 | 85 |
| 2  | 160 | 109 | 140 | 151 | 172 | 170 | 168 | 165 | 180 | 110 | 75 |
| 3  | 160 | 107 | 143 | 151 | 181 | 180 | 172 | 165 | 180 | 230 | 95 |
| 4  | N/A | —   | —   | —   | —   | —   | —   | —   | —   | —   | —  |
| 5  | 160 | 100 | 142 | 151 | 168 | 170 | 171 | 165 | 184 | 100 | 64 |
| 6  | 160 | 98  | 140 | 150 | 162 | 170 | 168 | 165 | 183 | 90  | 55 |
| 7  | 160 | 99  | 138 | 149 | 167 | 170 | 169 | 165 | 182 | 70  | 49 |
| 8  | 160 | 97  | 139 | 150 | 169 | 170 | 170 | 165 | 182 | 120 | 60 |
| 9  | 160 | 108 | 135 | 150 | 168 | 170 | 172 | 165 | 182 | 110 | 45 |
| 10 | 160 | 105 | 133 | 151 | 171 | 170 | 168 | 165 | 181 | 80  | 50 |
| 11 | 160 | 106 | 140 | 150 | 166 | 170 | 170 | 165 | 182 | 260 | 55 |
| 12 | 160 | 109 | 136 | 150 | 171 | 170 | 171 | 165 | 182 | 200 | 53 |
| 13 | 160 | 106 | 138 | 152 | 168 | 170 | 168 | 165 | 181 | 110 | 40 |
| 14 | 160 | 91  | 129 | 160 | 187 | 190 | 178 | 144 | 171 | 70  | 44 |
| 15 | 160 | 88  | 130 | 161 | 187 | 190 | 179 | 145 | 171 | 80  | 43 |
| 16 | 160 | 87  | 129 | 159 | 188 | 190 | 176 | 145 | 171 | 60  | 33 |
| 17 | 160 | 87  | 131 | 161 | 189 | 190 | 177 | 145 | 173 | 60  | 43 |
| 18 | 160 | 96  | 127 | 160 | 188 | 190 | 178 | 145 | 171 | 50  | 35 |
| 19 | 160 | 88  | 132 | 160 | 186 | 190 | 184 | 145 | 171 | 50  | 40 |
| 20 | 160 | 93  | 130 | 161 | 191 | 189 | 179 | 145 | 171 | 70  | 45 |
| 21 | —   | —   | —   | —   | —   | —   | —   | —   | —   | —   | —  |
| 22 | —   | —   | —   | —   | —   | —   | —   | —   | —   | —   | —  |

TABLE 3

Properties of the Compositions

| Example | Melt Flow Index (g/10 minutes) | Peak Stress (MPa) | % Elongation at break | Modulus (MPa) | Water Disintegration Time (minutes) |
|---|---|---|---|---|---|
| 1 | 25  | —  | —   | —    | —  |
| 2 | 29  | —  | —   | —    | 60 |
| 3 | 1.9 | —  | —   | —    | —  |
| 4 | 7   | —  | —   | —    | —  |
| 5 | 24  | 45 | 0.8 | 6550 | 55 |
| 6 | 39  | 54 | 2   | 4850 | 50 |

TABLE 3-continued

Properties of the Compositions

| Example | Melt Flow Index (g/ 10 minutes) | Peak Stress (MPa) | % Elongation at break | Modulus (MPa) | Water Disintegration Time (minutes) |
|---|---|---|---|---|---|
| 7  | 59  | 30 | 31  | 2500 | 45  |
| 8  | 18  | 31 | 83  | 2200 | 65  |
| 9  | 28  | 25 | 127 | 683  | 60  |
| 10 | 42  | 21 | 127 | 364  | 55  |
| 11 | 8   | 25 | 127 | 310  | —   |
| 12 | 10  | 23 | 127 | 270  | 105 |
| 13 | 22  | 16 | 127 | 122  | 120 |
| 14 | 147 | 15 | 48  | 288  | 35  |
| 15 | 142 | —  | —   | —    | —   |
| 16 | 62  | 26 | 47  | 1928 | 45  |
| 17 | 56  | 23 | 63  | 1343 | 50  |
| 18 | 140 | 14 | 67  | 226  | 50  |
| 19 | 90  | 22 | 40  | 931  | 45  |
| 20 | 134 | 16 | 46  | 347  | 40  |
| 21 | —   | 15 | 109 | 165  | 50  |
| 22 | —   | 13 | 80  | 174  | 45  |

As shown above, when SELVOL™ 502 low viscosity (3.0 to 3.7 cps) partially hydrolyzed polyvinyl alcohol was utilized and the plasticizer content was adjusted to 5 wt. %, 7 wt. %, 9 wt. %, 11 wt. % 13 wt. %, and 15 wt. %, the melt flow rate increased linearly from 24 grams per 10 minutes for the 5 wt. % glycerin up to 147 grams per 10 minutes for the 15 wt. % glycerin, as shown in Samples 5, 6, 7, 14, 19, and 20. Meanwhile, when SELVOL™ 203 high viscosity (3.5 to 4.5 cps) partially hydrolyzed polyvinyl alcohol was utilized and the plasticizer content was adjusted to 9 wt. %, 11 wt. %, and 13 wt. %, the melt flow rate also increased from 18 grams per 10 minutes to 28 grams per 10 minutes to 42 grams per 10 minutes, as shown in Samples 8, 9, and 10, although the melt flow rate was not as high as that observed for the SELVOL™ 502 low viscosity partially hydrolyzed polyvinyl alcohol for the same weight percent of plasticizer. For instance, with 9 wt. % plasticizer, the SELVOL™ 502 had a melt flow rate of 59 grams per 10 minutes 1.5 (Sample 7), while the SELVOL™ 203 had a melt flow rate of just 18 grams per 10 minutes (Sample 8). Further, when SELVOL™ 205 high viscosity (5.2 to 6.2 cps) partially hydrolyzed polyvinyl alcohol was utilized and the plasticizer content was adjusted to 13 wt. %, 15 wt. % and 20 wt. %, the melt flow rate also increased, as shown in Samples 11, 12, and 13. However, the overall melt flow rate was less than that for the SELVOL™ 502 and 203 at the same weight percent of plasticizer. For example, at 13 wt. %, the SELVOL™ 502 had a melt flow rate of 134 grams per 10 minutes (Sample 20), the SELVOL™ 203 had a melt flow rate of 42 grams per 10 minutes (Sample 10), and the SELVOL™ 205 had a melt flow rate of 8 grams per 10 minutes (Sample 11). Further, when the ratio of SELVOL™ 502 to any of the other polyvinyl alcohols was 1 or less (e.g., Sample 3), the resulting composition had a melt flow rate that was too low for injection molding (e.g., 1.9 grams per 10 minutes). Further, in many instances when only one polyvinyl alcohol polymer was utilized, the melt flow rate was less than 40 grams per 10 minutes (Samples 1-6, 8-9, and 11-13), which is not ideal for a thermoplastic, injection moldable composition. On the other hand, it was surprisingly found that combining a low viscosity polyvinyl alcohol polymer (e.g., SELVOL™ 502) with a higher viscosity polyvinyl alcohol polymer (e.g., SELVOL™ 203 and/or 205) resulted in a much higher melt flow rate greater than 40 grams/10 minutes, such as greater than 50 grams/10 minutes or higher, as shown in (Samples 15-18 and 21-22).

Turning now to the mechanical properties, it is first noted that properties for Examples 3 and 4 were not determined because the samples could not be injection molded. Further, it is observed that increasing the weight percentage of glycerin can reduce the modulus regardless of the viscosity of the partially hydrolyzed polyvinyl alcohol utilized, which corresponds with a more ductile, less brittle material. In addition, increasing the weight percentage of glycerin can also reduce the peak stress observed. Moreover, increasing the glycerin content can also increase the peak elongation. Further, by adjusting the weight percentage of glycerin as well as the combination of partially hydrolyzed polyvinyl alcohols (low and high viscosity) utilized, the modulus, peak stress, and peak elongation can be adjusted to levels similar to those of the propylene and linear low density polyethylene tampon applicator control samples, even though the samples of the present invention are also capable of being dispersed in water.

Additionally, the water disintegration test shows that despite having mechanical properties comparable to conventional tampon applicators, the tampon applicators formed from the thermoplastic composition of the present invention can also be water dispersible, unlike conventional tampon applicators.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A flushable tampon applicator, the tampon applicator comprising an outer tube for housing a tampon and comprising an inner tube, at least a portion of which extends into the outer tube, wherein the outer tube includes an outer, body-contacting surface, wherein the inner tube is moveable relative to the outer tube and configured to expel a tampon from the outer tube, further wherein at least one of the outer tube and the inner tube comprises a thermoplastic composition, the thermoplastic composition comprising:

from about 50 wt. % to about 98 wt. % of partially hydrolyzed polyvinyl alcohols, the partially hydrolyzed polyvinyl alcohols comprising a first polyvinyl alcohol, a second polyvinyl alcohol, and a third polyvinyl alcohol, wherein the viscosity of the first polyvinyl alcohol is less than the viscosity of the second polyvinyl alcohol, wherein the weight percentage ratio of the first polyvinyl alcohol to the second polyvinyl alcohol ranges from about 1 to about 20, wherein the first polyvinyl alcohol and the second polyvinyl alcohol each have a degree of hydrolysis ranging from about 80 mole % to about 90 mole %, and wherein the third polyvinyl alcohol has a viscosity that is greater than the viscosity of the first polyvinyl alcohol and the second polyviny alcohol; and from about 2 wt. % to about 50 wt. % of a plasticizer; wherein at least one of the outer tube and the inner tube is a molded part.

2. The tampon applicator of claim 1, wherein the first polyvinyl alcohol has a viscosity ranging from about 1 centipoise to about 3.5 centipoise and the second polyvinyl alcohol has a viscosity ranging from about 3.5 centipoise to about 15 centipoise.

3. The tampon applicator of claim 1, wherein the weight percentage ratio of the second polyvinyl alcohol to the third polyvinyl alcohol ranges from about 1 to about 10.

4. The tampon applicator of claim 1, wherein the tampon applicator has a peak elongation of from about 40% to about 200%.

5. The tampon applicator of claim 1, wherein the tampon applicator has a modulus of from about 100 MPa to about 2000 MPa.

6. The tampon applicator of claim 1, wherein the plasticizer is a polyhydric alcohol.

7. The tampon applicator of claim 6, wherein the plasticizer is a polyol.

8. The tampon applicator of claim 6, wherein the plasticizer is glycerol.

9. The tampon applicator of claim 1, wherein the body-contacting surface of the outer tube includes a water-insoluble material.

10. The tampon applicator of claim 9, wherein the ratio of the weight percentage of the water-insoluble material to the thermoplastic composition ranges from about 0.005 to about 1.

11. The tampon applicator of claim 9, wherein the water-insoluble material comprises a wax, silicon, polytetrafluoroethylene, polyethylene, a polyester, polyamide, a thermoplastic elastomer, or a combination thereof.

12. The tampon applicator of claim 1, wherein the thermoplastic composition has a melt flow rate of from about 40 grams per 10 minutes to about 160 grams per 10 minutes when subjected to a load of 2160 grams at a temperature of 190° C. according to ASTM Test Method D1238-E.

13. The tampon applicator of claim 1, wherein the tampon applicator is injection molded.

14. The tampon applicator of claim 1, wherein the tampon applicator disintegrates in tap water in less than about 18 hours, wherein the tap water has a temperature of less than about 25° C.

15. A method for forming an injection molded part, the method comprising:
    injection molding a pelletized, water-dispersible, thermoplastic composition into a mold cavity, wherein the thermoplastic composition comprises from about 50 wt. % to about 98 wt. % of partially hydrolyzed polyvinyl alcohols, the partially hydrolyzed polyvinyl alcohols comprising a first polyvinyl alcohol, a second polyvinyl alcohol, and a third polyvinyl alcohol, wherein the viscosity of the first polyvinyl alcohol is less than the viscosity of the second polyvinyl alcohol, wherein the weight percentage ratio of the first polyvinyl alcohol to the second polyvinyl alcohol ranges from about 1 to about 20, wherein the first polyvinyl alcohol and the second polyvinyl alcohol each have a degree of hydrolysis ranging from about 80 mole % to about 90 mole %, and wherein the third polyvinyl alcohol has a viscosity that is greater than the viscosity of the first polyvinyl alcohol and the second polyvinyl alcohol; and from about 2 wt. % to about 50 wt. % of a plasticizer, wherein the composition has a melt flow rate of from about 40 grams per 10 minutes to about 160 grams per 10 minutes when subjected to a load of 2160 grams at a temperature of 190° C. according to ASTM Test Method D1238-E; and
    shaping the thermoplastic composition into a molded part within the mold cavity.

16. The method of claim 15, wherein the first polyvinyl alcohol has a viscosity ranging from about 1 centipoise to about 3.5 centipoise and the second polyvinyl alcohol has a viscosity ranging from about 3.5 centipoise to about 15 centipoise.

17. The method of claim 15, wherein the weight percentage ratio of the second polyvinyl alcohol to the third polyvinyl alcohol ranges from about 1 to about 10.

18. The method of claim 15, further comprising a co-injection molding process, wherein the injection molded part is a two layered molded part having an inner layer and an outer layer, wherein the inner layer comprises the injection-molded, thermoplastic composition and the outer layer is water-insoluble.

19. The method of claim 18, wherein the outer layer comprises from about 1 wt. % to about 50 wt. % of the injection molded part and the inner layer comprises from about 50 wt. % to about 99 wt. % of the injection molded part.

20. The method of claim 18, wherein the outer layer comprises a wax, silicon, polytetrafluoroethylene, polyethylene, a polyester, polyamide, a thermoplastic elastomer, or a combination thereof.

21. The method of claim 15, wherein the molded part is a tampon applicator.

* * * * *